United States Patent [19]
Milá-de-la-Roca et al.

[11] 4,318,992
[45] Mar. 9, 1982

[54] FERMENTER

[75] Inventors: Yolanda M. Milá-de-la-Roca; Beltran V. Azuaje; Omar R. Gil, all of Caracas, Venezuela

[73] Assignee: Instituto Nacional de Higiene Rafael Rangel, Caracas, Venezuela

[21] Appl. No.: 154,961

[22] Filed: May 30, 1980

[51] Int. Cl.$^3$ .............................................. C12M 1/34
[52] U.S. Cl. ................................. 435/291; 422/101; 435/311; 435/313
[58] Field of Search ........................ 71/9, 10; 210/180; 422/88, 99, 101, 119; 435/284, 286, 287, 289, 290, 291, 292, 294, 311, 800, 807, 813, 819

[56] References Cited
U.S. PATENT DOCUMENTS

| | | | |
|---|---|---|---|
| 1,244,995 | 10/1917 | Loomis | 210/180 |
| 2,672,053 | 3/1954 | Geyer | 422/99 |
| 3,172,235 | 3/1965 | Bjorklund | 435/289 |
| 3,219,319 | 11/1965 | Ash | 435/813 |
| 3,607,737 | 9/1971 | Gamer | 210/613 |
| 3,715,298 | 2/1973 | Goodson et al. | 435/817 |
| 3,926,738 | 12/1975 | Nyiri et al. | 435/289 |
| 4,116,778 | 9/1978 | Belousov et al. | 435/813 |
| 4,167,450 | 9/1979 | Chesbro et al. | 435/289 |

Primary Examiner—Peter A. Hruskoci
Attorney, Agent, or Firm—Karl F. Ross

[57] ABSTRACT

A fermenter, suitable for use in the production of biological materials is, constituted by a fermenter container, connected a seeder, a sampler, a harvester and a gas-decontaminating and venting system for gases produced within the apparatus. The fermenter container can also be provided with a heater, as well as a magnetic shaker and a support therefor.

3 Claims, 2 Drawing Figures

FERMENTER

FIELD OF THE INVENTION

The present invention relates to a fermentation apparatus, suitable for the production of biological materials, such as toxoids, vaccines and cultures.

BACKGROUND OF THE INVENTION

It is already known to produce biological materials by fermentation in a static or bulk-fermentation method. This method involves the inoculation of a suitable culture medium, maintained under such conditions and temperature as to provide for the reproduction thereof. This method has the disadvantage of limited production so that a series of static units are necessary, in order to obtain a significant output. Therefore, some years ago, this method was replaced by an improved fermentation method capable of producing substantially increased amounts of products compared to the space and time necessary with the prior static method.

It is however a disadvantage of this fermentation method that, in order to carry out the same, it was necessary to provide a series of units at high investment and maintenance cost. Additionally it was necessary to rely upon highly specialized conditions, and skilled labor. As a consequence thereof, in the presence of a shortage of parts for the apparatus, any damage to a portion thereof resulted in the stoppage of the production until the malfunctioning element or damaged part could be acquired and the entire system would be returned to its optimal production condition.

OBJECT OF THE INVENTION

It is the object of this invention to provide an improved fermentation apparatus, suitable for the production of toxoids, vaccines, cultures and other biological products, which is simple in assembling and manipulation, of extremely low initial and maintainance cost, and the assembling of which does not require of high technology.

SUMMARY OF THE INVENTION

The apparatus of the invention comprises a fermentation container, connected in a closed system to a seeding device, a sampling device, a harvesting device and a gas decontaminating and venting system for those gases produced within the fermenter apparatus. Additionally, this apparatus is made up by a series of connecting devices, mainly in the form of a series of tubes and tubings, all suitable to carry biological materials and the derivatives thereof. Furthermore, the apparatus of this invention is also constituted by heating means for the fermenter container agitating or shaking means and supporting means therefor.

SPECIFIC DESCRIPTION

Figure 1:
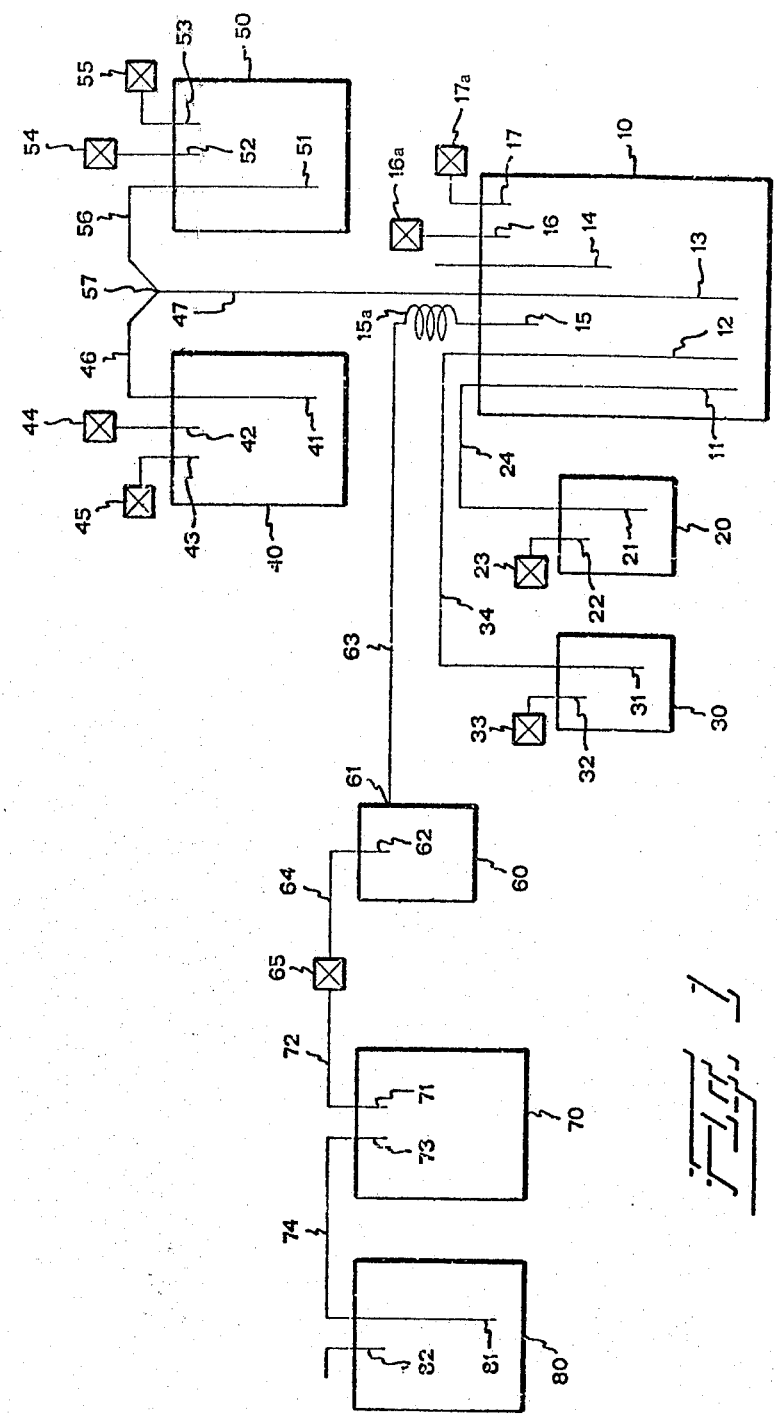
FIG. 1 is a block diagram illustrating the various devices constituting the apparatus of this invention as well as the interconnection thereof.

As above stated, the fermentation apparatus of this invention is basically constituted by a fermentation container 10 in which the reaction or reactions are to be effected. These reactions can be the formation of a culture, or the production of biological products, such as toxoids, vaccines, etc. The container is of a suitable size, composed of a biological inert material, closed by closure means through which a seeding tube passes as shown at 11, arranged to extend down to the bottom of the container 10, and through which the inoculation of the biological substance to be treated in the apparatus is effected. A second tube 12, identical with the first one, also extends through the closure means down to the bottom of the container 10 and enables the sampling of the product. A third tube 13 is a harvesting tube, with a diameter substantially greater than said tubes 11 and 12 is arranged to extend also through the closure down to the bottom of the container 10. Furthermore, a tube 14, with its lower end closed, is provided through said closure extending down to a short distance from said closure. Within said tube 14, a thermometer 14a (see FIG. 2) is provided, in order to monitor continuously the temperature inside the container 10, during the entire culturing or the like process.

Also extending a short distance from the closure another tube 15 is provided to extend down a short distance within said container 10, and the top end of which is connected or constituted by, a coil 15a, suitable for condensing the water vapor or steam produced within said container 10.

A pair of additional tubes 16 and 17 pass through said closure and extend a short distance within said container 10. The respective top end of the tubes 16 and 17 are provided, respectively, with air-filters 16a and 17a, in order to avoid contamination on venting from the container 10.

Figure 2:
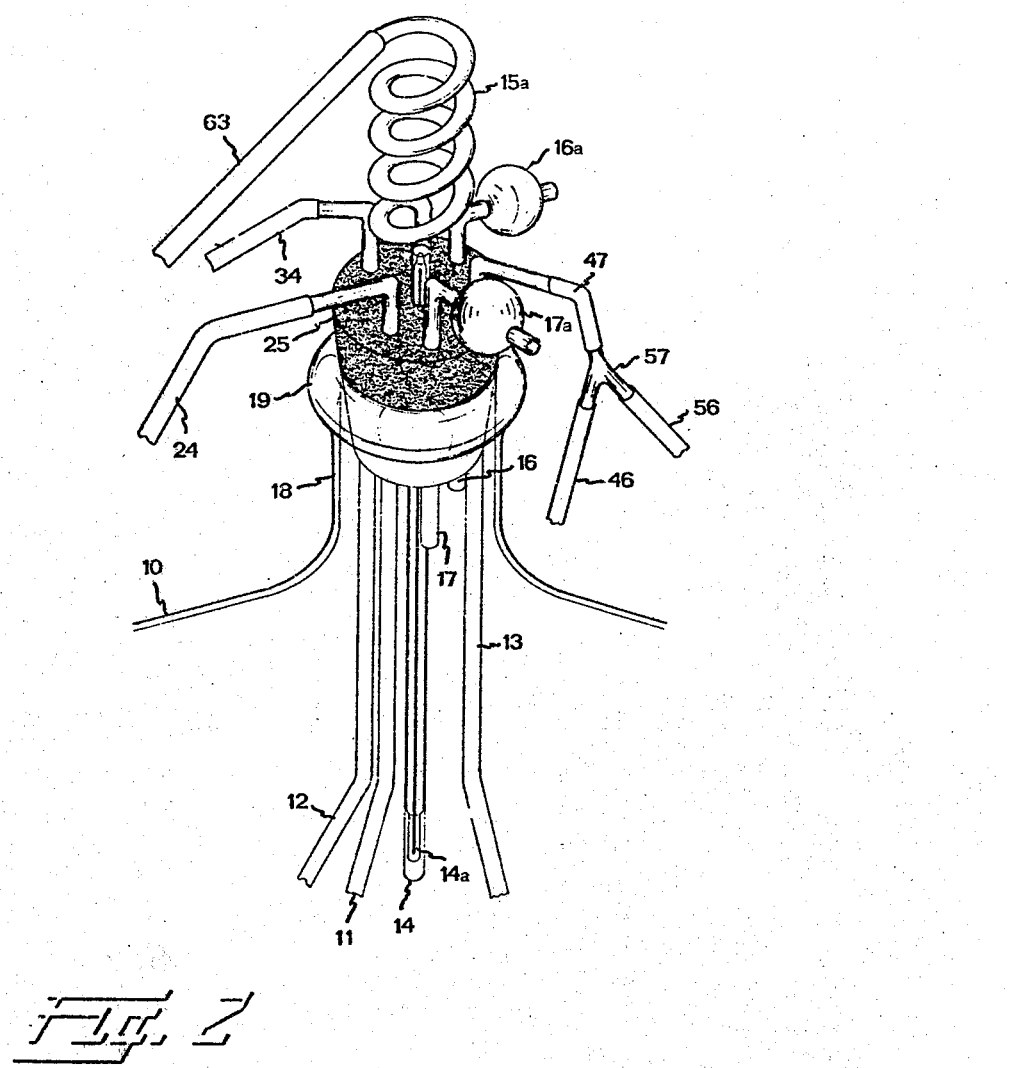
FIG. 2 is a detailed view in a conventional top portion of a fermentation container used in this invention.

As clearly seen in FIG. 2, said container 10 could be constituted as a high-volume flask, the top end of which ends in a neck 18 forming a mouth 19. Said mouth 19 is provided with a stopper 25 or another closure means, through which the above disclosed series of tubes and conduits will pass into said container or flask 10. Of course, both the flask 10 and the tubes and conduits are made of biological inert material.

Externally of the flask and said closure means 25, additional connecting elements extend as described hereinbelow. Seeding tube 11 of said container 10 is connected to a seeding flask 20, which also can be a glass flask of smaller dimensions than said flask 10. The flask 20 is also provided with a closure means, through which a first tube 21 passes and extends down to the bottom of said container 20. The top end of said tube 21 is connected to the seeding tube 11 of said container 10, by means of a tubing 24. A second tube 22 passes also through this closure means of the seeding container 20, and is provided exteriorly with an air filter 23 to avoid contamination or for air venting. The lower end of said tube 22 ends at short distance from said closure means.

The sampling tube 12 of the container 10 is connected to a sampling container 30. Preferably, said container 30 is a common assay tube, provided with a stopper or similar closure means, through which a first tube 31, is passed. The tube 31 is connected, by means of the tubing 34, to the sampling tube 12 of said container 10. A second tube 32 passes through said closure means of the assay tube 30 and the lower end thereof ends at short distance from said closure means, while the top end thereof is provided, exteriorly to said container 30, with an air filter 33, in order to avoid contaminated air venting and in order to provide an easy to operate connection to positive or negative pressure source, as needed.

The tube 13 of the container 10 is connected to a couple of harvesting containers 40, 50. Both containers are preferably alike and made of biologically inert material. The container 40 is constituted preferably by a flask of relatively smaller size than container 10, and provided with a closure means through which a first tube 41 passes and proceeds down to the bottom of said container 40. Two additional tubes 42 and 43 are provided exteriorly with air filters 44, 45, respectively, in order to avoid air venting without decontamination and provide an easy-to-operate connection to positive or negative pressure sources, as needed. The tube 41 and a similar tube 51 for container 50, are connected by means of respective conduits or tubings 46, 56, to an intermediate "Y"-shaped connector 57 which, in turn, is coupled by means of a tubing 47, to the tube 13 of container 10. The container 50 is also provided with two additional tubes 52 and 53 which, like tubes 42 and 43 of said container 40, enter a short distance within the respective container 50, and are externally provided with air-filters 54, 55, respectively, in order to avoid contaminated-air venting and provide an easy-to-operate connection to positive or negative pressure source, as needed.

Finally, tube 15 of container 10, externally provided with coil 15a, is connected to a system suitable for gas decontamination and venting. This system is made up by a first container 60, provided with a side entrance 61 which, by means of a conduct or tubing 63 is connected to said coil 15a. At the top end of said container 60, a closure member is provided, through which a first tube 62 passes to a short distance within said container 60. Said tube 62, by means of a tubing 64, is connected to an air filter 65, intermediate to said container 60 and a second container 70.

The container 70 is of greater size than the container 60 and, as a third container 80, and the first container 60, are made of biologically inert materials. Said second and third containers 70 and 80 are serially connected to each other. Said container 70 is provided only with top closure, through which a first tube 71 passes to a short distance within said container and is connected, by means of the tubing 72, to the air filter 65. A second tube 73 is passed approximately to the same distance within the container and is exteriorly connected by means of a tubing 74, to a first tube 81 entering said container 80 down to the bottom thereof. The container 80 is designed to contain a suitable amount of a caustic substance, preferably a volume of a 10N sodium hydroxide water solution, the level of which is to be made higher than the lower end of said tube 81.

A second tube 82 constitutes an atmosphere vent for the gaseous by-products formed at the apparatus, mainly at the fermentation container 10. The gases, before exiting through said tube 82, are bubbled from said tube 81, through said caustic solution provided at said container 80.

It is preferred that all the elements forming the fermenter apparatus of this invention are of the easy available type forming laboratory stock. Thus, as containers 10, 20, 40, 50, 70 and 80, Erlenmeyer flasks can be employed, while as container 60 a side-arm flask can be used, the side opening of which is to be connected by means of said tubing 63, to the coil 15a. Also, as container 30, as above stated, a standard assay tube can be used. The tubes, tubings and connectors mentioned above can be made of glass or stainless steel. The connection of one tube to another or to a tubing is made preferably with rubber connectors.

The manipulation of the apparatus of this invention is highly simple, easy to obtain, even for sterilizing the same. All elements are sterilized together, except for harvesting containers 40, 50, which are sterilized apart by employing measures tending to avoid contamination, for instance, by covering ends of tubes and rubber connectors with gauze. For containers 10–80 a sterilization time of one hour at about 121° C. is recommended. Prior to the sterilization stage and the connection of all elements one to another, in the array shown by FIG. 1, a magnetic bar (not shown) is introduced into container 10 together with the culture medium and then said tubes 11, 12 and 13 are provisionally closed down.

By the magnetic agitator and a heating unit, the agitation and suitable temperature are obtained within said container 10. The progress of said temperature is to be monitored by means of the thermometer 14a (FIG. 2). When a suitable temperature, preferably about 35° C. is obtained and is steady, a sample can be taken in order to check the pH.

If the pH and temperature factors are satisfactory, the seeding of the fermentation container 10 can be effected. To this end, a flask containing the inoculum can be coupled to the seeding system 20, and vaccum is applied through one of said filters 16a, 17a. When enough vaccum is obtained, the communication between container 20 and container 10 is opened so that the culture broth can be passed into the bottom of said container 10. When the above operation is finished, the tube 11 is closed again, and the vaccum source is disconnected. Then, the decontamination and venting system 60–80 is connected by opening the path through said tube 15.

At predetermined intervals after the seeding, air will be passed through said fermentor in order to expell those gases produced therein. To this end, one of the filters 16a, 17a is connected to a compressed air net. Of course, the remaining air filter must be shut down.

The production medium is thus controlled and, after a predetermined fermentation time, samples can be taken in order to check the production. When sampling is to be effected, a container 30 is employed which, until now, was closed relative to the remainder of the apparatus. So, communication is established between said container 30 and the tube 12, in order that the air pressure existing within said container 10 drives a sample into the container 30. When said sample is of the desired volume, the tube 12 is closed, and this step is repeated as often as desired or convenient. When two successive samples give the same value, the reaction will be considered as ended, and harvesting can begin.

To this end, first the connection to the gas decontamination and venting is closed and then, through the seeding system a chemical substance is applied to the product, suitable to obtain the detoxification of the system. Then, the connection between containers 40–50 and said container 10 is opened, and simultaneously vaccum is applied to the containers 40–50 through one of the filters 44, 45 or 54, 55, leaving the other filter of each couple as a safety valve. Once the harvesting is ended, the vaccum is disconnected and the connection to the containers 40–50 is closed. These containers and the tubes and tubings connecting them to the system are to be replaced before the same or another biological product is harvested.

What is claimed is:

1. A fermentation apparatus comprising:

a fermentation container formed with a closure at the top thereof and adapted to receive a culture medium;

a first tube extending through said closure into said container and terminating at an upper portion of said container while being connected to a condenser coil for condensing water vapor formed in said container and returning the condensed water vapor thereto;

a decontamination and venting system connected to said coil and including a vessel containing a caustic solution and at least one further vessel disposed between the caustic solution vessel having tubes opening into the top thereof and respectively communicating with said coil and with said caustic solution vessel below the level of the caustic solution therein;

temperature monitoring means extending through said closure into said vessel;

a second tube extending through said closure into said vessel, provided with an air filter and connectable to a source of fluid pressure operable to draw material into said container or drive material from said container;

a third tube extending through said closure into said container and extending substantially to the bottom thereof;

a harvesting system including a pair of vessels connected to said third tube for receiving material displaced by fluid pressure through said third tube;

a fourth tube extending through said closure into said container substantially to the bottom thereof and connected to a sampling vessel; and a fifth tube extending through said closure substantially to the bottom of said container and connected to a seeding vessel adapted to receive an inoculum for said medium and enable said inoculum to be transferred to said container through said fifth tube, said harvesting, sampling and seeding vessels each being provided with air filters adapted to be connected to said source.

2. The apparatus defined in claim 1 wherein said decontamination and venting system comprises a further vessel having a side opening connected to said coil, a tube connected through an air filter between the top of the latter vessel and said further vessel of said system, said caustic solution vessel being vented to the atmosphere.

3. The apparatus defined in claim 2 wherein said seeding and sampling vessels are assay tubes.

* * * * *